(12) United States Patent
Mallampalli

(10) Patent No.: US 7,230,091 B2
(45) Date of Patent: Jun. 12, 2007

(54) CCT PROTEIN EXPRESSION PROMOTER

(75) Inventor: Rama K. Mallampalli, Solon, IA (US)

(73) Assignee: University of Iowa Research Foundation, Iowa City, IA (US)

(*) Notice: Subject to any disclaimer, the term of this patent is extended or adjusted under 35 U.S.C. 154(b) by 97 days.

(21) Appl. No.: 10/488,438

(22) PCT Filed: Sep. 5, 2001

(86) PCT No.: PCT/US01/27428

§ 371 (c)(1),
(2), (4) Date: Sep. 20, 2004

(87) PCT Pub. No.: WO03/022862

PCT Pub. Date: Mar. 20, 2003

(65) Prior Publication Data

US 2005/0054069 A1    Mar. 10, 2005

(51) Int. Cl.
    *C07H 21/04*     (2006.01)
(52) U.S. Cl. .................. 536/24.1; 435/6; 435/193; 435/252.3; 435/320.1; 536/23.1
(58) Field of Classification Search ............... 536/24.1, 536/23.1; 435/6, 193, 252.3, 320.1
    See application file for complete search history.

(56) References Cited

OTHER PUBLICATIONS

Accession No. AF092568.*
Accession No. U84199.*
Adelman et al., "In Vitro Deletional Mutagenesis for Bacterial Production of the 20,000-Dalton Form of Human Pituitary Growth Hormone," *DNA*, 1983, 2(3):183-193.
Altschul et al., "Gapped BLAST and PSI-BLAST: a new generation of protein database search programs," *Nucleic Acids Res.*, 1997, 25(17):3389-3402.
Altschul et al., "Basic Local Alignment Search Tool," *J. Mol. Biol.*, 1990, 215:403-410.
An, "Binary Ti Vectors for Plant Transformation and Promoter Analysis," *Meth. Enzymol.*, 1987, 153:292-305.
Bakovic et al., "Transcriptional activation of the murine CTP:phosphocholine cytidylyltransferase gene (Ctpet): combined action of upstream stimulatory and inhibitory cis-acting elements," *Biochim. Biophys. Acta*, 1999, 1438:147-165.
Carter et al., "Both Erk and p38 Kinases Are Necessary for Cytokine Gene Transcription," *Am. J. Respir. Cell Mol. Biol.*, 1999, 20:751-758.
Choi et al., "Cloning of CTP:Phosphocholine Cytidylyltransferase cDNA from *Arabidopsis thaliana*," *Mol. Cells*, 1997, 7(1):58-63.
Corpet, "Multiple sequence alignment with hierarchical clustering," *Nucl. Acids Res.*, 1988, 16(22):10881-10890.
Crea et al., "Chemical synthesis of genes for human insulin," *Proc. Natl. Acad. Sci. U.S.A.*, 1978, 75(12):5765-5769.
Goeddel et al., "Synthesis of human fibroblast interferon by *E. coli*," *Nucleic Acids Res.*, 1980, 8(18):4057-4074.
Higgins and Sharp, "Fast and sensitive multiple sequence alignments on a microcomputer," *CABIOS*, 1989, 5(2):151-153.
Higgins and Sharp, "CLUSTAL: a package for performing multiple sequence alignment on a microcomputer," *Gene*, 1988, 73:237-244.
Huang et al., "Parallelization of a local similarity algorithm," *CABIOS*, 1992, 8(2):155-165.
Joshi, "An inspection of the domain between putative TATA box and translation start site in 79 plant genes," *Nucl. Acid Res.*, 1987, 15(16):6643-6653.
Kalmar et al., "Cloning and expression of rat liver CTP:phosphocholine cytidylyltransferase: An amphipathic protein that controls phosphatidylcholine synthesis," *Proc. Natl. Acad. Sci. USA*, 1990, 87:6029-6033.
Kalmar et al., "Primary structure and expression of a human CTP:phosphocholine cytidylyltransferase," *Biochim. Biophys. Acta*, 1994, 1219:328-334.
Karlin and Altschul, "Methods for assessing the statistical significance of molecular sequence features by using general scoring schemes," *Proc. Natl. Acad. Sci. USA*, 1990, 87:2264-2268.
Karlin and Altschul, "Applications and statistics for multiple high-scoring segments in molecular sequences," *Proc. Natl. Acad. Sci. USA*, 1993, 90:5873-5877.
Lawn et al., "The sequence of human serum albumin cDNA and its expression in *E. coli*," *Nucl. Acids Res.*, 1981, 9(22):6103-6114.
Lykidis et al., "Cloning and Characterization of a Second Human CTP:Phosphocholine Cytidylyltransferase," *J. Biol. Chem.*, 1998, 273(22):14022-14029.
Mallampalli et al., "Tumor Necrosis Factor-α Inhibits Expression of CTP:Phosphocholine Cytidylyltransferase," *JBC*, 2000, 275(13):9699-9708.
Meinkoth and Wahl, "Hybridization of Nucleic Acids Immobilized on Solid Supports," *Anal. Biochem.*, 1984, 138:267-284.
Myers and Miller, "Optimal alignments in linear space," *CABIOS*, 1988, 4(1):11-17.
Needleman and Wunsch, "A General Method Applicable to the Search for Similarities in the Amino Acid Sequence of Two Proteins," *J. Mol. Biol.*, 1970, 48:443-453.
Nishida et al., "Cloning of *Brassica napus* CTP:phosphocholine cytidylyltransferase cDNAs by complementation in a yeast *cct* mutant," *Plant Mol. Biol.*, 1996, 31:205-211.
Pearson and Lipman, "Improved tools for biological sequence comparison," *Proc. Natl. Acad. Sci. USA*, 1988, 85:2444-2448.
Pearson, "Using the FASTA Program to Search Protein and DNA Sequence Databases," *Meth. Mol. Biol.*, 1994 24:307-331.
Rutherford, et al., "The Gene for Murine CTP:Phosphocholine Cytidylyltransferase(*Ctpct*) Is Located on Mouse Chromosome 16," *Genomics*, 1993, 18:698-701.
Smith and Waterman, "Comparison of Biosequences," *Adv. App. Math.*, 1981, 2:482-489.

(Continued)

*Primary Examiner*—Tekchand Saidha
(74) *Attorney, Agent, or Firm*—Viksnins Harris & Padys PLLP

(57) ABSTRACT

The present invention provides a noveal isolated and purified nucleic acid molecule having a nucleotide sequence that in nature directs transcription of CTP:phosphocholine cytidylyltrransferase (CCT), i.e., is a novel CCT promoter, and methods of use thereof.

18 Claims, 9 Drawing Sheets

OTHER PUBLICATIONS

Sweitzer and Kent, "Expression of Wild-Type and Mutant Rat Liver CTP:Phosphocholine Cytidylyltransferase in a Cytidylyltransferase-Deficient Chinese Hamster Ovary Cell Line," *Arch. Biochem. Biophys.*, 1994, 311(1):107-116.

Tang et al., "The Structure of the Gene for Murine CTP: Phosphocholine Cytidylyltransferase, Ctpct," *J. Biol. Chem.*, 1997, 272(20):13146-13151.

Tijssen, "Overview of principles of hybridization and the strategy of nucleic acid probe assays," *Laboratory Techniques in Biochemistry and Molecular Biology-Hybridization with Nucleic Acid Probes*, Part I, chapter 2, Elsevier, New York, 1993, pp. 19-78.

Tsukagoshi et al., "Molecular cloning and characterization of the gene encoding cholinephosphate cytidylyltransferase in *Saccharomyces cerevisiae*," *Eur. J Biochem.*, 1987, 169:477-486.

Turner and Foster, "The Potential Exploitation of Plant Viral Translational Enhancers in Biotechnology for Increased Gene Expression," *Mol. Biotech.*, 1995, 3:225-236.

Vieira and Messing, "Production of Single-Stranded Plasmid DNA," *Meth. Enzymol.*, 1987, 153:3-11.

Yeo et al., "Molecular cloning of CTP:phosphocholine cytidylyltransferase from *Plasmodium falciparum*," *Eur. J. Biochem.*, 1995, 233:62-72.

* cited by examiner

SEQUENCE LISTING

<160> NUMBER OF SEQ ID NOS: 8

<210> SEQ ID NO 1
<211> LENGTH: 208
<212> TYPE: DNA
<213> ORGANISM: Mus musculus

<400> SEQUENCE: 1

```
ccctctggaa gcggaactac tctgtcaggt tgtggttttc aggaatgcgg aggtggcatt      60
gacaagaggg cgggcgggag gcgggacttc cggtccgcag tccggtcaga tgtttcccgg     120
gcgtctcccc gcaacccatt tgacttcgct agtcggtgac gcggcgcggg gaagggatcc     180 gaggggacc ggagcctgga ggagttga                                         208
```

<210> SEQ ID NO 2
<211> LENGTH: 243
<212> TYPE: DNA
<213> ORGANISM: Artificial Sequence
<220> FEATURE:
<223> OTHER INFORMATION: A mutated CCTp240 promoter

<400> SEQUENCE: 2

```
agcgttcggc tcagtaaacc cacgcgcccg gcccctctgg aagcggaact actactctgt      60
caggttgtgg ttttcaggaa tgcggaggtg gcattgacaa gagggcgggc gggaggcggg     120
acttccggtc cgcagtccgg tcagatgttt cccggcgtc tccccgcaac ccatttgact     180 cgctagtcg gtgacgcggc gcgggaagg gatccgaggg ggaccggagc ctggaggagt     240
tga                                                                   243
```

<210> SEQ ID NO 3
<211> LENGTH: 20
<212> TYPE: DNA
<213> ORGANISM: Mus musculus

<400> SEQUENCE: 3

```
ccctctggaa gcggaactac                                                  20
```

<210> SEQ ID NO 4
<211> LENGTH: 21
<212> TYPE: DNA
<213> ORGANISM: Mus musculus

<400> SEQUENCE: 4

```
tcaactcctc caggctccgg t                                                21
```

<210> SEQ ID NO 5
<211> LENGTH: 10
<212> TYPE: DNA
<213> ORGANISM: Mus musculus

<400> SEQUENCE: 5

```
gtcaccccac                                                             10
```

```
<210> SEQ ID NO 6
<211> LENGTH: 10
<212> TYPE: DNA
<213> ORGANISM: Artificial Sequence
<220> FEATURE:
<223> OTHER INFORMATION: A mutated putative sterol regulatory element
      within the 5' flanking region of the CCT gene

<400> SEQUENCE: 6
gtaaacccac                                                            10

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ccgctcagta aacccacgcg cccgg                                           25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
ccgggcgcgt gggtttactg agccg                                           25
```

CCT PROTEIN EXPRESSION PROMOTER

The invention was made with the support of NIH Grant No. R01 HL 55584. The U.S. government has certain rights in the invention.

FIELD OF INVENTION

The present invention relates generally to the field of molecular biology. More specifically, it relates to the regulation of gene expression.

BACKGROUND OF INVENTION

Promoters and other regulatory components from bacteria, viruses, fungi and animals have been used to control gene expression in animal cells. Numerous transformation experiments using DNA constructs comprising various promoter sequences fused to various foreign genes, such as bacterial marker genes, have led to the identification of useful promoter sequences.

The limitations of currently available eukaryotic promoters include the fact that they lack sufficient activity when used to induce expression of proteins, are too large to be packaged into adenoviral vectors for in vivo gene delivery, or succumb to promoter "turn-off" by inflammatory factors elaborated by the host. In addition, such promoters are often based on sequences obtained from viruses.

There is, therefore, an unmet need for a eukaryotic promoter that exhibits robust activity with several fold greater activity than the presently known promoters.

SUMMARY OF INVENTION

The present invention provides an isolated and purified nucleic acid promoter molecule that in nature directs transcription of CTP:phosphocholine cytidylyltransferase (CCT), a key ubiquitous regulatory enzyme present in nucleated (eukaryotic) cells involved in phospholipid synthesis. This nucleotide sequence may be a CCTp208 promoter (SEQ ID NO:1) or a mutated CCTp240 promoter (mCCTp240) (SEQ ID NO:2). SEQ ID NO:1 is the following: CCCTCTGGAAGCGGAACTACTCTGTCAG-GTTGTGGTTTTCAGGAATGC GGAGGTGGCATTGA-CAAGAGGGCGGGCGGGAGGCGGGACTTCCGGT CCGCAGTCCGGTCAGATGTTTC-CCGGGCGTCTCCCCGCAACCCATTTG ACT-TCGCTAGTCGGTGACGCGGCGCGGG-GAAGGGATCCGAGGGGGA CCGGAGCCTGGAGGAGTTGA. SEQ ID NO:2 is the following: AGCGTTCGGCTCAGTAAACCCACGCGC-CCGGCCCCTCTGGAAGCGGA ACTACTCTGTCAG-GTTGTGGTTTTCAGGAATGCGGAGGTGGCATTGAC AAGAGGGCGGGCGGGAGGCGGGACTTC-CGGTCCGCAGTCCGGTCAG ATGTTTC-CCGGGCGTCTCCCCGCAAC-CCATTTGACTTCGCTAGTCGGT GACGCGGCGCGGGAAGGGATC-CGAGGGGGACCGGAGCCTGGAGGA GTTGA. The mutated CCTp240 is identical to the native CCTp240 sequence except that the putative sterol regulatory element region within the 5' flanking region (−156/−147) bp relative to the first transcriptional start site of the CCT gene has been mutated.

CCT promoters of the present invention confer high levels of expression of operably linked preselected DNA segments in eukaryotic cells, in particular in an animal cell, such as a mammalian cell. The nucleotide sequence of a promoter of the present invention may substantially identical to a polynucleotide encoded by SEQ ID NO:1 or SEQ ID NO:2 or a fragment (portion) of SEQ ID NO:1 or SEQ ID NO:2, and is biologically active. In other words, the present invention includes promoters that are substantially similar to SEQ ID NO:1 or SEQ ID NO:2. Another embodiment of the invention is a CCTp208 or mCCTp240 promoter that comprises the minimum number of contiguous nucleotides that initiate RNA transcription.

CCT promoters of the present invention exhibit at least about a 2-fold increase in expression above a PGL3Pro promoter. The promoter may exhibit at least about a 10-fold, 20-fold, or even 30-fold increase in expression about a PGL3Pro promoter.

Also provided are compositions, expression cassettes (e.g., recombinant vectors), and host cells, comprising the nucleic acid molecule that comprises a nucleic acid segment that encodes a CCTp208 or mCCTp240. In one embodiment, the invention provides an expression cassette or vector containing an isolated nucleic acid molecule having a CCTp208 or mCCTp240 promoter nucleotide sequence that directs transcription of a linked nucleic acid segment in a cell, which nucleotide sequence is optionally operably linked to other suitable regulatory sequences, e.g., a transcription terminator sequence, operator, repressor binding site, transcription factor binding site and/or an enhancer. This expression cassette or vector may be contained in a host cell. The expression cassette or vector may augment the genome of a host cell or may be maintained extrachromosomally. The expression cassette may be operatively linked to a structural gene, an open reading frame thereof, or a portion thereof.

The present invention further provides a method of augmenting a eukaryotic genome by contacting a eukaryotic cell with a nucleic acid molecule of the invention, e.g., one having a CCTp208 or mCCTp240 promoter nucleotide sequence that directs transcription of a linked nucleic acid segment so as to yield a transformed eukaryotic cell. The nucleic acid molecule may be present inside or outside the nucleus, such as in the mitochondria of the cell.

The present invention also provides host cells made by the method described above.

The present invention further provides host cells containing the a CCTp208 or mCCTp240 promoter described above, or the expression cassettes described above.

DETAILED DESCRIPTION OF THE INVENTION

Figure 1A:
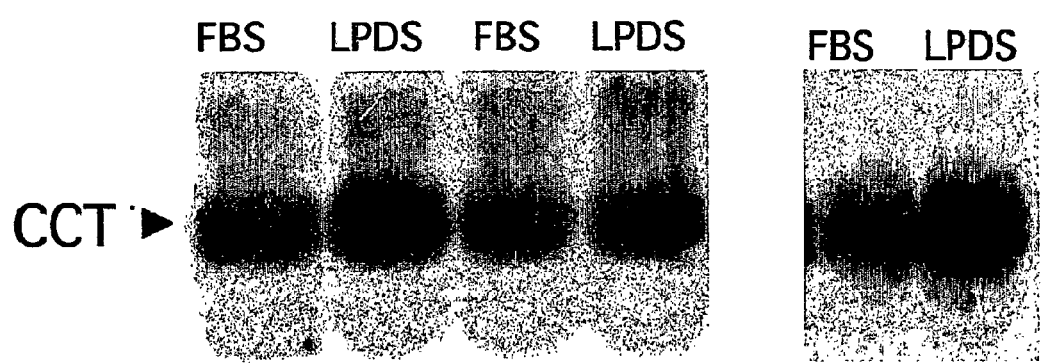
FIG. 1 shows the effect of LPDS on CCT mRNA in MLE cells. (A) CCT mRNA or (13)18S RNA was determined by Northern analysis. (C) CCT mRNA levels in FBS and LPDS exposed cells as determined by Northern analysis using poly(A)-rich RNA. (D) Densitometric analysis of CCT mRNA in cells.
Figure 1B:
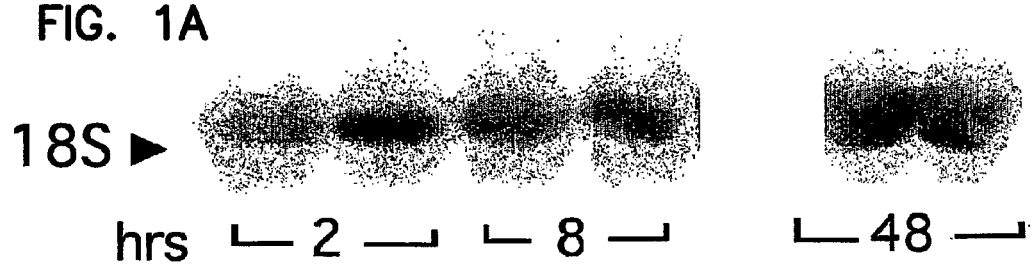
Figure 1C:
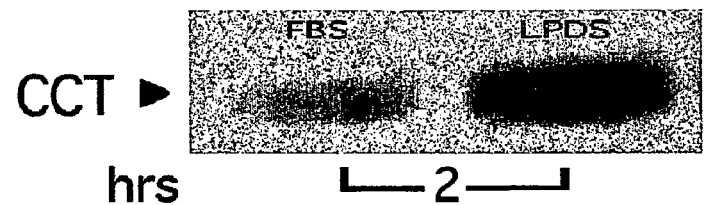
Figure 1D:
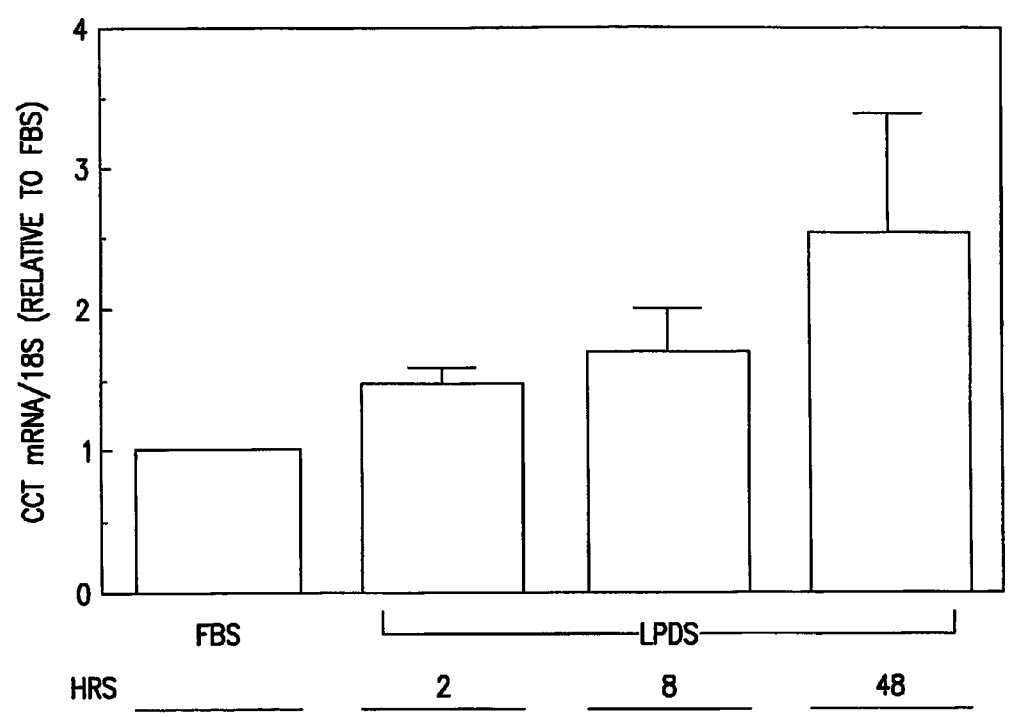

Phosphatidylcholine (PC) is the major structural phospholipid in all eukaryotic cells, including mammalian membranes, and plays a significant role in the production of intracellular messenger molecules. The biosynthesis of PC occurs mainly through the CDP-choline pathway, but in the liver PC is also made by the methylation of phosphatidylethanolamine. The rate of PC biosynthesis is governed tightly in most instances by the rate of conversion of phosphocholine to CDP-choline, a very slow (rate-limiting) reaction catalyzed by CTP:phosphocholine cytidylyltransferase (CCT). CCT activity is regulated by the reversible translocation between the membranes where it is active and a soluble form that has low activity. Enzyme-membrane interactions play an important role in the activation, and translocation to the membranes can be achieved either by dephosphorylation or by the presence of lipids. Protein phosphorylation/dephosphorlation may also be an important regulatory mechanism for the modulation of CCT activity and translocation, but a definitive demonstration of the specific kinases involved in vivo remains to be elucidated CCT purified from rat liver is a homodimer with a subunit molecular mass of 42 kDa. cDNAs for CCT have been cloned from yeast (Tsukagoshi et al., *Eur. J. Biochem.* (1987) 169:477–486), rat (Kalmar et al., *Proc. Nat'l Acad. Sci. USA* (1990) 87:6029–6033), CHO cells (Sweitzer et al., *Arch. Biochem. Biophys.* (1994) 311:207–226), HeLa cells (Kalmar et al., *Biochim. Biophys. Acta* (1994) 1219:328–334), mouse (Rutherford et al., *Genomics* (1993) 18:698–701), *Arabidopsis thaliana* (Choi et al., *Mol. Cells* (1997) 7:58–63), *Plasmodium falciparum* (Yeo et al., *Eur. J. Biochem.* (1995) 233:62–72), and *Brassica napus* (Hashida et al., *Plant Mol. Biol.* (1996) 316: 205–211). In humans two isoforms of CCT, CCT-alpha and CCT-beta, have been identified (Lykidis et al., *J. Biol. Chem.* (1998) 273:4022–14029).

A genomic clone containing the last two exons and the 3'-noncoding sequence of the murine CCT gene (Ctpct) was cloned (Rutherford et al., *Genomics* (1993)18:698–701). Ctpct was subsequently identified as a single copy gene located on mouse chromosome 16. Tang et al. isolated and characterized the entire coding region of the Ctpct gene (Tang et al., *J. Biol. Chem.* (1997) 272:13146–13151). Bakovic et al. reported the structural and functional organization of the 5'-flanking sequence of the Ctpct gene. They delineated several promoter regions involved in the activation and repression of transcription (Bakovic et al., *Biochem. Biophys. Acta* (1999) 1438:147–165). In particular, they studied the following regions of the mouse Ctpct promoter: −2068/−418, −2068/+38, −1268/+38, −210/+38, −130/+38, −90/+38, −52/+38, −10/+38, and +15/+38.

The present invention describes novel DNA sequences that encode a ubiquitous mammalian enzyme, CCT. The specific gene sequences discovered by the inventors were termed the CCTp208 and mCCTp240 promoters. These promoters significantly stimulate the expression of genes in a variety of cell types. The CCTp208 and mCCTp240 promoters exhibit robust activity with several fold greater activity, when compared to some existing viral promoters (e.g., the strong viral SV40 promoter). The relatively small size of these mammalian sequences allows for insertion into gene transfer vectors. These observations indicate that these CCT promoters may be uniquely significant making them useful in molecular biology (e.g., reporter gene expression) and protein engineering. The applications of these promoters include the generation of recombinant proteins, reporter gene expression, and incorporation of vectors used in gene delivery and immunization protocols.

These novel promoter sequences exhibit high levels of activity contained within a relatively small DNA region. These properties have three potential advantages compared to currently available promoters: (1) easy packaging into adenoviral vectors used to deliver genes exogenously, (2) ability to retain enhanced expression of desired genes and (3) since the CCT promoter is not a viral-based sequence, there is a potential to circumvent effects of inflammatory host response that turn off activity of commonly available promoters.

These gene sequences are potent and yet their activity is confined to a relatively small sequence of DNA and thus can be linked to a gene transfer vector (e.g., an adenovirus) to drive the expression of other genes used to express proteins in a stable fashion. These CCT promoters exhibit a 31-fold increase in expression above a comparable, currently available commercial promoter, PGL3Pro, when tested using lung cells (Promega, Inc.)

Definitions

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative. Some mammalian promoters, such as the CCT promoter, have two transcription initiation sites.

Promoter elements, particularly a TATA element, that are inactive or that have greatly reduced promoter activity in the absence of upstream activation are referred to as "minimal" or "core" promoters. In the presence of a suitable transcription factor, the minimal promoter functions to permit transcription. A minimal or core promoter thus consists only of all basal elements needed for transcription initiation, e.g., a TATA box and/or an initiator.

As used herein, the term "CCT promoter" means a nucleotide sequence, which when operably linked to a preselected DNA segment that encodes a protein, RNA transcript, or mixture thereof, results in the expression of the linked preselected DNA segment. As used herein, the term CCT promoter includes the full-length CCTp208 and mCCTp240 promoter and biologically active subunits of these promoters. The term CCT promoter also includes sequences that are substantially identical to that of SEQ ID NO:1 and SEQ ID NO:2. Sequence comparisons maybe carried out using a Smith-Waterman sequence alignment algorithm (see e.g., Waterman (1995) or http://www hto.us-c.edu/software/seqaln/index.html). The localS program, version 1.16, can be preferably used with following parameters: match: 1, mismatch penalty: 0.33, open-gap penalty: 2, extended-gap penalty: 2.

A "portion," "fragment" or "subunit" of the promoters of the present invention is a sequence having at least about 50–70 nucleotides, at least about 100 nucleotides, at least about 150 nucleotides, at least about 208 nucleotides, or at least about 240 nucleotides, so as to confer promoter activity at a biologically active level.

As used herein, "biologically active" means that the promoter has at least about 0.1%, 10%, 25%, 50%, 75%, 80%, 85%, even 90% or more, e.g. 91%, 92%, 93%, 94%, 95%, 96%, 97%, 98%, 99% or 100% of the activity of the CCT promoter comprising SEQ ID NO:1 or SEQ ID NO:2. The activity of a promoter can be determined by methods well known to the art. For example, see Sambrook et al., Molecular Cloning: A Laboratory Manual (1989). Promoters of the present invention that are not identical to SEQ ID NO:1 or SEQ ID NO:2, but retain comparable biological activity, are called variant promoters. The nucleotide sequences of the invention include both naturally occurring sequences as well as recombinant forms.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. A "nucleic acid fragment" is a fraction of a given nucleic acid molecule. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The invention encompasses isolated or substantially purified nucleic acid compositions. In the context of the present invention, an "isolated" or "purified" DNA molecule is a nucleic acid molecule that exists apart from its native environment and is therefore not a product of nature. An isolated nucleic acid molecule may exist in a purified form or may exist in a non-native environment such as, for example, a transgenic host cell. For example, an "isolated" or "purified" nucleic acid molecule, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (ie., sequences located at the 5' and 3' ends of the nucleic acid) in the genomic DNA of the organism from which the nucleic acid is derived. For example, in various embodiments, the isolated nucleic acid molecule can contain less than about 70 bp, 50 bp, 10 bp, or even 5 bp, 4 bp, 3 bp, 2 bp or 1bp of nucleotide sequences that naturally flank the nucleic acid molecule in genomic DNA of the cell from which the nucleic acid is derived. By "fragment" or "portion" is meant a full length or less than full length of the nucleotide sequence.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Naturally occurring" is used to describe an object that can be found in nature as distinct from being artificially produced. For example, a nucleotide sequence present in an organism (including a virus) that can be isolated from a source in nature and has not been intentionally modified by man in the laboratory, is "naturally occurring."

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

"Recombinant DNA molecule" is a combination of DNA sequences that are joined together using recombinant DNA technology and procedures used to join together DNA sequences as described, for example, in Sambrook et al., Cold Spring Harbor, N.Y.: Cold Spring Harbor Laboratory Press (1989).

A "vector" is defined to include, inter alia, any plasmid, cosmid, phage or binary vector in double or single stranded linear or circular form that may or may not be self transmissible or mobilizable, and can transform prokaryotic or eukaryotic host either by integration into the cellular genome or exist extrachromosomally (e.g., autonomous replicating plasmid with an origin of replication).

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Such expression cassettes will comprise the transcriptional initiation region linked to a nucleotide sequence of interest. Such an expression cassette may be provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Regulatory sequences" and "suitable regulatory sequences" each refer to nucleotide sequences located upstream (5' non-coding sequences), within, or downstream (3'non-coding sequences) of a coding sequence, and influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995)).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more nucleic acids: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (ie., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al, *Gene*, 73:237 (1988); Higgins et al, *CABIOS*, 5:151 (1989); Corpet et al, *Nucl. Acids Res.*, 16:10881 (1988); Huangetal., *CABIOS*, 8:155 (1992); and Pearson et al, *Meth. Mol Biol*, 24:307 (1994). The ALIGN program is based on the algorithm of Myers and Miller, supra. The BLAST programs of Altschul et al, *JMB*, 215:403 (1990); *Nucl. Acids Res.*, 25:3389 (1990), are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.*, 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e) The terms "substantial identity" or "substantially identical" when referring to polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500 µL; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 1° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, N.Y. (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g. about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook et al., Molecular Cloning: A Laboratory Manual (2d ed., Cold Spring Harbor Laboratory Press, Plainview, N.Y.) (1989). See also Inis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Significant increase" is an increase that is larger than the margin of error inherent in the measurement technique, preferably an increase by about 2-fold or greater.

I. Recipient Cells

The present invention employs recipient eukaryotic cells that are susceptible to transformation. Such cells can be of plant or animal origin, such as mammalian cells. For example, studies testing the CCTp208 promoter utilized transformed murine lung epithelial cell lines (MLE-12), human adenocarcinoma lung cell lines (A549), a hepatoma cell line (HepG2), and immortalized fetal rat lung alveolar epithelial cell lines (IFT2).

Nutrients are provided to the cell cultures in the form of media and the environmental conditions for the cultures are controlled. Media and environmental conditions that support the growth of cell cultures are well known to the art.

II. DNA Sequences

Virtually any DNA composition may be used for delivery to recipient cells in accordance with the present invention. The DNA segment or gene chosen for cellular introduction will often encode a protein and can be expressed in the resultant transformed cells. The DNA segment or gene chosen for cellular introduction may also encode anti-sense RNA, i.e., a complement of a predetermined RNA molecule, or a portion thereof, that is expressed in an untransformed cell. The transcription of an anti-sense RNA suppresses the expression of the complementary RNA, e.g., one that encodes an undesirable property. Thus, a preselected DNA segment, in the form of vectors and plasmids, or linear DNA fragments, in some instances containing only the DNA element to be expressed in the eukaryote may be employed.

A replicating vector may also be useful for delivery of a target gene. Examples of useful vectors include pGL2-Basic Vector (firefly luciferase) from Promega, pCAT3-Basic Vector (CATransferase) from Promega. or a pSEAP2 Vector (secreted alkaline phosphatase) from Clontech.

DNA useful for introduction into cells includes that which has been derived or isolated from any source, that may be subsequently characterized as to structure, size and/or function. An example of such DNA "isolated" from a source would be a useful DNA sequence that is excised or removed from a source by chemical means, e.g., by the use of restriction endonucleases, so that it can be further manipulated, e.g., separated or amplified, e.g., via polymerase chain reaction (PCR), for use in the invention, by the methodology of genetic engineering. Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9:6103 (1981), and Goeddel et al., *Nucleic Acids Res.*, 8:4057 (1980). Thus, DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

An example of DNA "derived" from a source, would be a DNA sequence or segment that is identified as a useful fragment within a given organism, and that is then chemically synthesized in essentially pure form. Therefore, "recombinant or preselected DNA" includes completely synthetic DNA sequences, semi-synthetic DNA sequences, DNA sequences isolated from biological sources, and DNA sequences derived from RNA, as well as mixtures thereof.

The introduced DNA includes, but is not limited to, DNA from genes such as those from bacteria, yeasts, animals, plants or viruses. Moreover, it is within the scope of the invention to isolate a preselected DNA segment from a given genotype, and to subsequently introduce multiple copies of the preselected DNA segment into the same genotype, e.g., to enhance production of a given gene product. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or DNA sequences or segments that are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, that can also contain coding regions flanked by regulatory sequences that promote the expression of the recombinant DNA present in the resultant transformed cell.

Generally, the introduced DNA will be relatively small, i.e., less than about 30 kb to minimize any susceptibility to physical, chemical, or enzymatic degradation that is known to increase as the size of the DNA increases. As noted above, the number of proteins, RNA transcripts or mixtures thereof, encoded by the DNA molecules that are introduced into the genome is preferably preselected and defined, e.g., from one to about 5–10 such products of the introduced DNAs may be formed.

A. Preparation of an Expression Cassette

An expression cassette of the invention can comprise a recombinant DNA molecule containing a preselected DNA segment operably linked to a CCTp208 or mCCTp240 promoter functional in a host cell. The expression cassette itself may be chimeric, i.e., the cassette comprises DNA from at least two different species, or comprises DNA from the same species, and is linked or associated in a manner that does not occur in the "native" or wild type of the species.

1. DNA Molecules of the Invention That Comprise a CCT Promoter of the Present Invention A promoter is a region of DNA that regulates gene expression. Promoter regions are typically found in the flanking DNA sequence upstream from the coding sequence in viruses as well as prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

The DNA molecule of the invention comprises a preselected DNA segment comprising a CCTp208 (such as SEQ ID NO:1) or mCCTp240 promoter (such as SEQ ID NO:2) that is operably linked to a preselected DNA segment that a person would like expressed. The desired preselected DNA segment can be combined with the CCT promoter by standard methods as described in Sambrook et al., *Molecular Cloning: A Laboratory Manual*, Cold Spring Harbor (1989)). Briefly, the preselected DNA segment can be subcloned downstream from the promoter using restriction enzymes to ensure that the DNA is inserted in proper orientation with respect to the promoter so that the DNA can be expressed. Once the preselected DNA segment is operably linked to the promoter, the expression cassette so formed can be subcloned into a plasmid or other vector.

2. Variants of the DNA Molecules of the Invention

Nucleic acid molecules encoding nucleotide sequence variants of a CCTp208 promoter (e.g., SEQ ID NO:1) or an mCCTp240 promoter (e.g. SEQ ID NO:2), can be prepared by a variety of methods known in the art. These methods include, but are not limited to, isolation from a natural source (in the case of naturally occurring nucleotide sequence variants) or preparation by oligonucleotide-mediated (or site-directed) mutagenesis, PCR mutagenesis, and cassette mutagenesis of an earlier prepared variant or a non-variant version of the CCT promoter of the present invention.

Oligonucleotide-mediated mutagenesis is a preferred method for preparing nucleotide substitution variants of the CCT promoter. This technique is well known in the art as described by Adelman et al., *DNA*, 2:183 (1983). Briefly, CCT promoter DNA is altered by hybridizing an oligonucleotide encoding the desired mutation to a DNA template, where the template is the single-stranded form of a plasmid or bacteriophage containing the unaltered or native DNA sequence of the CCT promoter. After hybridization, a DNA polymerase is used to synthesize an entire second complementary strand of the template that will thus incorporate the oligonucleotide primer, and will code for the selected alteration in the CCT promoter.

Generally, oligonucleotides of at least about 20–25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75:5765 (1978).

The DNA template can be generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.*; 153:3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the CCT promoter, and the other strand (the original template) encodes the native, unaltered sequence of the CCT promoter. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}P$ to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above.

A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

Embodiments of the invention include an isolated and purified DNA molecule comprising a preselected DNA segment comprising a CCTp208 promoter comprising SEQ ID NO:1 or mCCTp240 promoter comprising SEQ ID NO:2, or nucleotide sequence variants of SEQ ID NO:1 or SEQ ID NO:2 that retain the biological activity of the promoter.

3. Optional Sequences in the Expression Cassette

The expression cassette can also optionally contain other DNA sequences. In order to improve the ability to identify transformants, one may desire to employ a selectable or screenable marker gene as, or in addition to, the expressible preselected DNA segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait that one can 'select' for by chemical means, i.e., through the use of a selective agent (e.g., an antibiotic), or whether it is simply a trait that one can identify through observation or testing. Of course, many examples of suitable marker genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA; small active enzymes detectable in extracellular solution.

Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques that are known in the art, the present invention renders possible the introduction of any gene, including marker genes, into a recipient cell.

Transcription enhancers or duplications of enhancers can be used to increase expression from a particular promoter. Also, leader sequences that influence gene expression may be used. These are DNA sequences inserted between the transcription initiation site and the start of the coding sequence, i.e., the untranslated leader sequence. Preferred leader sequence include those that comprise sequences selected to direct optimum expression of the attached gene, i.e., to include a preferred consensus leader sequence that can increase or maintain mRNA stability and prevent inappropriate initiation of translation (Joshi, *Nucl. Acid Res.*, 15:6643 (1987)). Such sequences are known to those of skill in the art. However, some leader sequences have a high degree of secondary structure that is expected to decrease mRNA stability and/or decrease translation of the mRNA. Thus, leader sequences that do not have a high degree of secondary structure or that have a high degree of secondary structure where the secondary structure does not inhibit mRNA stability and/or decrease translation will be most preferred. Other such regulatory elements useful in the practice of the invention are known to those of skill in the art.

Additionally, expression cassettes can be constructed and employed to target the gene product of the preselected DNA segment to an intracellular compartment within cells or to direct a protein to the extracellular environment. This can generally be achieved by joining a DNA sequence encoding a transit or signal peptide sequence to the coding sequence of the preselected DNA segment. The resultant transit, or signal, peptide will transport the protein to a particular intracellular, or extracellular destination, respectively, and can then be post-translationally removed. Transit or signal peptides act by facilitating the transport of proteins through intracellular membranes, e.g., mitochondrial membranes, whereas signal peptides direct proteins through the extracellular membrane. By facilitating transport of the protein into compartments inside or outside the cell, these sequences can increase the accumulation of gene product.

It may be useful to target DNA itself within a cell. For example, it may be useful to target an introduced preselected DNA to the nucleus as this may increase the frequency of transformation. Within the nucleus itself, it would be useful to target a gene in order to achieve site-specific integration. For example, it would be useful to have a gene introduced through transformation replace an existing gene in the cell.

When the expression cassette is to be introduced into a cell, the expression cassette can also optionally include 3' nontranslated regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains transcriptional and translational termination sequences. These 3' nontranslated regulatory sequences can be obtained as described in An, *Methods in Enzymology*, 153:292 (1987) or are already present in plasmids available from commercial sources such as Clontech, Palo Alto, Calif. The 3' nontranslated regulatory sequences can be operably linked to the 3' terminus of the preselected DNA segment.

An expression cassette can also be introduced into an expression vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Thus, additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

III. DNA Delivery

The expression cassette or vector can be introduced into a recipient cell to create a transformed cell. A preselected DNA segment may be delivered into cells or tissues, by currently available methods including, but not limited to, infectious viruses, the use of liposomes, microinjection by mechanical or laser beam methods, by whole chromosomes or chromosome fragments, and electroporation.

The invention will be further described by the following examples.

EXAMPLE 1

Type II alveolar epithelial cells critically rely on lipids carried within circulating lipoproteins to adequately synthesize the surfactant lipid, disaturated phosphatidylcholine (DSPtdCho). Studies have not investigated feedback control mechanisms by which these cells maintain surfactant PtdCho homeostasis under conditions of lipid (sterol) deprivation.

Prior studies showed that fasting or lipid restriction in animal models transiently decreases surfactant levels and surface-activity, however levels are restored by 96 hrs. Fasting increases choline incorporation into DSPtdCho suggesting that PtdCho synthesis increases a compensatory mechanism in response to caloric restriction. CTP: phosphocholine cytidylyltransferase (CCT) is the rate-limiting enzyme involved in DSPtdCho synthesis, and CCT activity is stimulated by long-term lipoprotein deprivation. Also, published sequence information for the mouse CCT gene (Bakovic et al., *BBA*, 1438:147–65, 1999) indicates several potential binding sites (SP 1, SRE) that might confer sterol regulation.

The present studies were conducted primarily using a murine alveolar type II epithelial cell line (MLE-12). Cells were cultured in Hites medium with 10% fetal bovine serum (FBS) or 10% lipoprotein-deficient serum (LPDS) supplemented with lovastatin (2 μg/ml) or cyclodextrin (100

μg/ml) for 72 hrs prior to analysis. Northern Blotting was performed as described using CCTA specific probes (Mallampalli et al., *JBC:* 275:9699–9708, 2000). Amplification of varying portions of the proximal 5' flanking region of the mouse CCT gene (CCTp298) was performed using PCR using mouse genomic DNA as a template. A pCR 4-TOPO cloning vector (In Vitrogen) and the reporter vector, pGL3 Basic (Promega), were used to generate CCT promoter-reporter constructs for transient transfections to assess reporter activity. Specifically, a proximal 5' region of the gene was amplified by PCR using C57B1/6J mouse genomic DNA (100 ng) as a template. Primers (0.4 μM) 5'-CCCTCTGGAAGCGGAACTAC-3' (left) (SEQ ID NO:3) and 5'-TCAACTCCTCCAGGCTCC-GGT-3' (right) (SEQ ID NO:4) were incubated in a reaction mixture using PCR Supermix (Life Technologies) containing 1.5 mM MgCl 200 μM dNTP and Taq DNA polymerase (1.0 U/per 50 μl of reaction solution). PCR conditions included an initial cycle of 94° C. for 2 min, followed by 35 cycles at 94° C. for 30 sec, 56° C. for 30 sec, and 72° C. for 2 min plus final extension at 72° C. for 10 min. Amplification resulted in a 208 bp product that was then cloned into a pCR4-TOPO cloning vector (InVitrogen). The product was digested with Not1 and Spe1, gel purified, and sequenced. It was confirmed to be identical to the published sequence. This fragment was then directionally subcloned into a reporter construct (pGL3basic, Promega, Madison, Wis.) upstream of the firefly luciferase coding region. Expression was evaluated after transient transfection into a murine lung epithelial cell line (MLE) cultured in the presence of fetal bovine serum for 24 hrs.

Effect of LPDS on CCT mRNA in MLE cells (FIG. 1). Cells were grown in Hite's medium with 10% FBS for 72 hrs before changing to fresh medium containing 10% FBS or 10% LPDS for 2 to 48 h. As indicated in FIG. 1, at the indicated times, total cellular RNA (50 μg) was isolated and the amount of (A) CCT mRNA or (B) 18S RNA was determined by Northern analysis. Representative autoradiograms are shown. (C) CCT mRNA levels in FBS and LPDS exposed cells as determined by Northern analysis using 10 μg poly(A)-rich RNA. (D) Densitometric analysis of CCT mRNA in cells cultured in medium containing 10% FBS or 10% LPDS for 2 to 48 hrs. The CCT mRNA/18S ratios for FBS were arbitrarily assigned a value of 1. The densitometric data is from 3 independent experiments. Values are shown as mean±SEM.

Figures 2A, 2B:
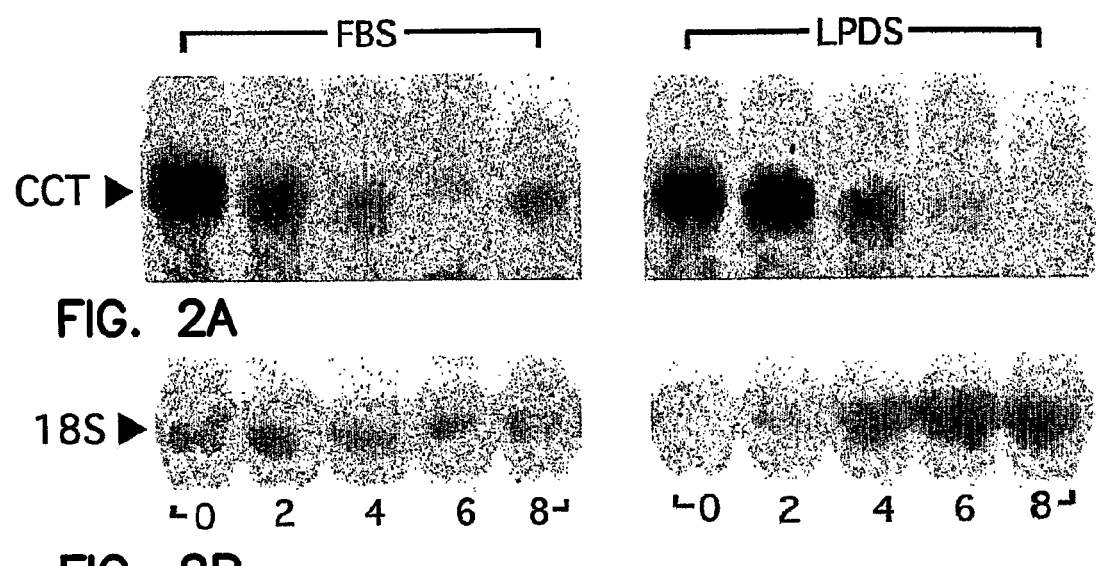
FIG. 2 shows the effect of LPDS on turnover of CCT mRNA in MLE cells. Northern analysis of total cellular RNA (A) CCT mRNA and (B) 18S RNA. (C) Densitometric analysis of autoradiograms shows CCT mRNA/18S OD ratios.
Figure 2C:
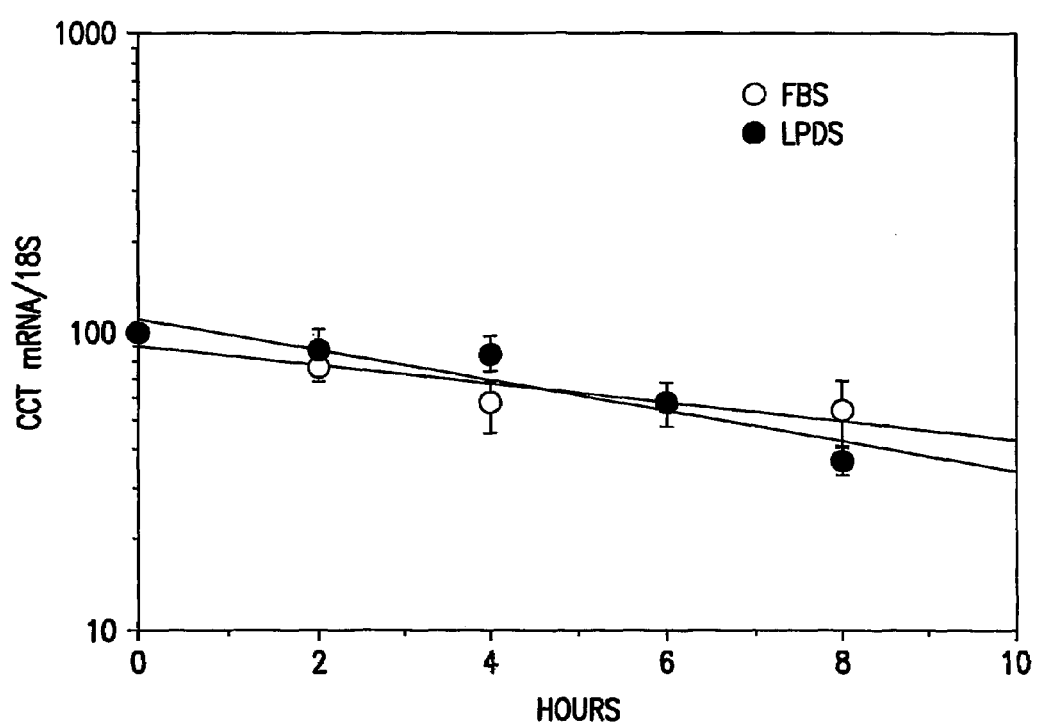

The effect of LPDS on turnover of CCT mRNA in MLE cells (FIG. 2). Cells were grown in Hite's medium containing 10% FBS for 72 hrs before changing to fresh medium with either 10% FBS or 10% LPDS containing 5 μg/ml actinomycin D for 0 to 8 hrs. Northern analysis of total cellular RNA (50 μg) was performed to determine amounts of (A) CCT mRNA and (B) 18S RNA. (C) Densitometric analysis of autoradiograms shows CCT mRNA/18S OD ratios for cells grown in medium containing 5 μg/ml actinomycin D with either 10% FBS or 10% LPDS. Values are expressed on a logarithmic scale and expressed as mean±SEM from 3 independent experiments.

Figure 3:
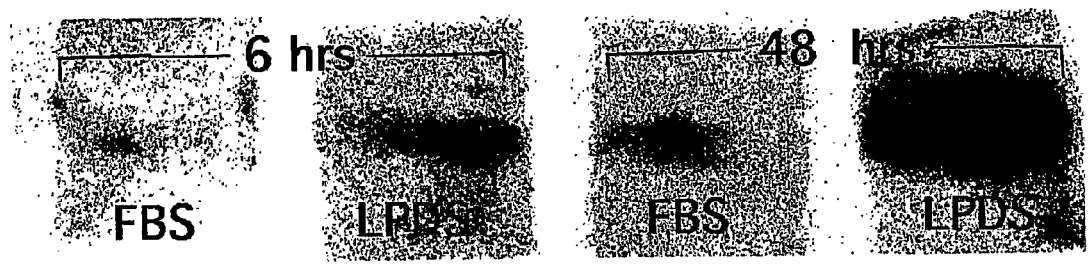
FIG. 3 shows the effect of LPDS on CCT gene transcription in MLE cells.

The effect of LPDS on CCT gene transcription in MLE cells (FIG. 3). Cells were grown in Hite's medium containing 10% FBS for 72 hrs before changing to fresh medium with either 10% FBS or 10% LPDS for 6 or 48 hrs. After culture, cells were harvested and processed for CCT transcriptional activity as described using a nuclear run on assay (*Am. J. Respir. Cell Mol. Biol.,* 20:751 (1999)). The data is representative of two independent experiments.

Figure 4:
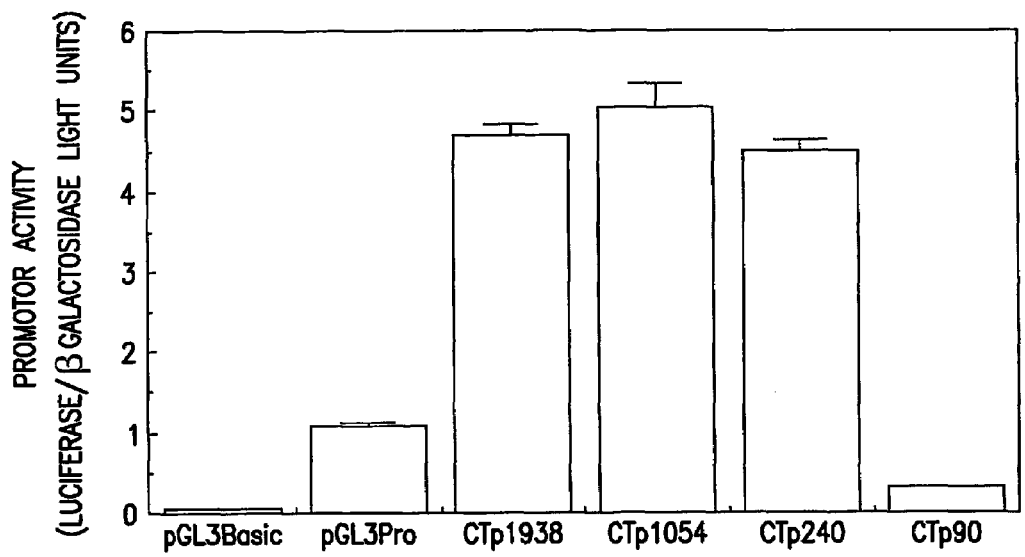
FIG. 4 shows deletional analysis of the CCT promoter in MLE cells.

Deletional Analysis of the CCT Promoter in MLE Cells (FIG. 4). Transfections were conducted in 0.5% Hites medium with Fugene 6 with 0.75 μg of test plasmid for 90 min using six different luciferase vectors: 1) PGL3 Basic, a negative control, contains no promoter; 2) PGL3 Promoter (PGL3 Pro), a positive control, contains the SV40 promoter, and 3) CCTp1938 (−1867/+71), CCTp1054 (−983/+71), CCTp240(−169/+71), and CCTp90 (−19/+71), the experimental vectors containing fragments of the CCT promoter cloned into PGL3 Basic. Immediately after transfections cells were exposed to medium containing 10% FBS for 18 hr. Luciferase and β-galactosidase activities in cellular extracts were determined by luminometer readings after these values were normalized for transfection efficiency by co-transfection with CMV-β-gal (0.25 μg). Data is from n=7 studies.

Figure 5:
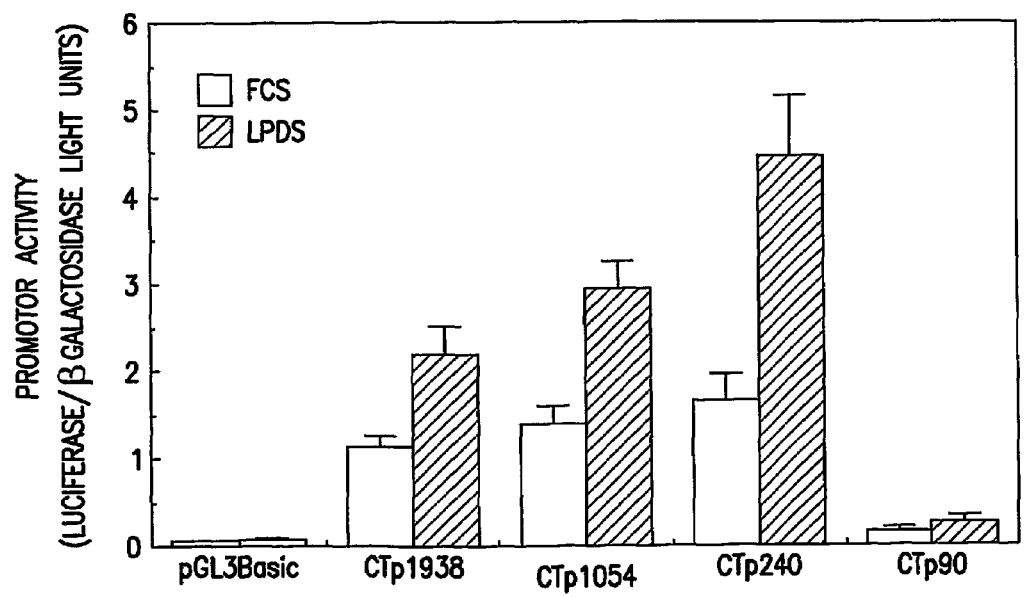
FIG. 5 shows that LPDS activates the CCT promoter in MLE cells.

LPDS Activates the CCT Promoter in MLE Cells (FIG. 5). Transfections were conducted as in FIG. 4 using PGL3 Basic, a negative control and CCTp1938, CCTp1054, CCTp240, and CCTp90 as experimental vectors. After transfections cells were exposed to medium containing 10% FBS or LPDS for 18 hr. Luciferase and β-galactosidase activities in cellular extracts were determined by luminometer readings after these values were normalized for transfection efficiency by co-transfection with CMV-β-gal. The data is representative of n=6 separate studies.

Figure 6:
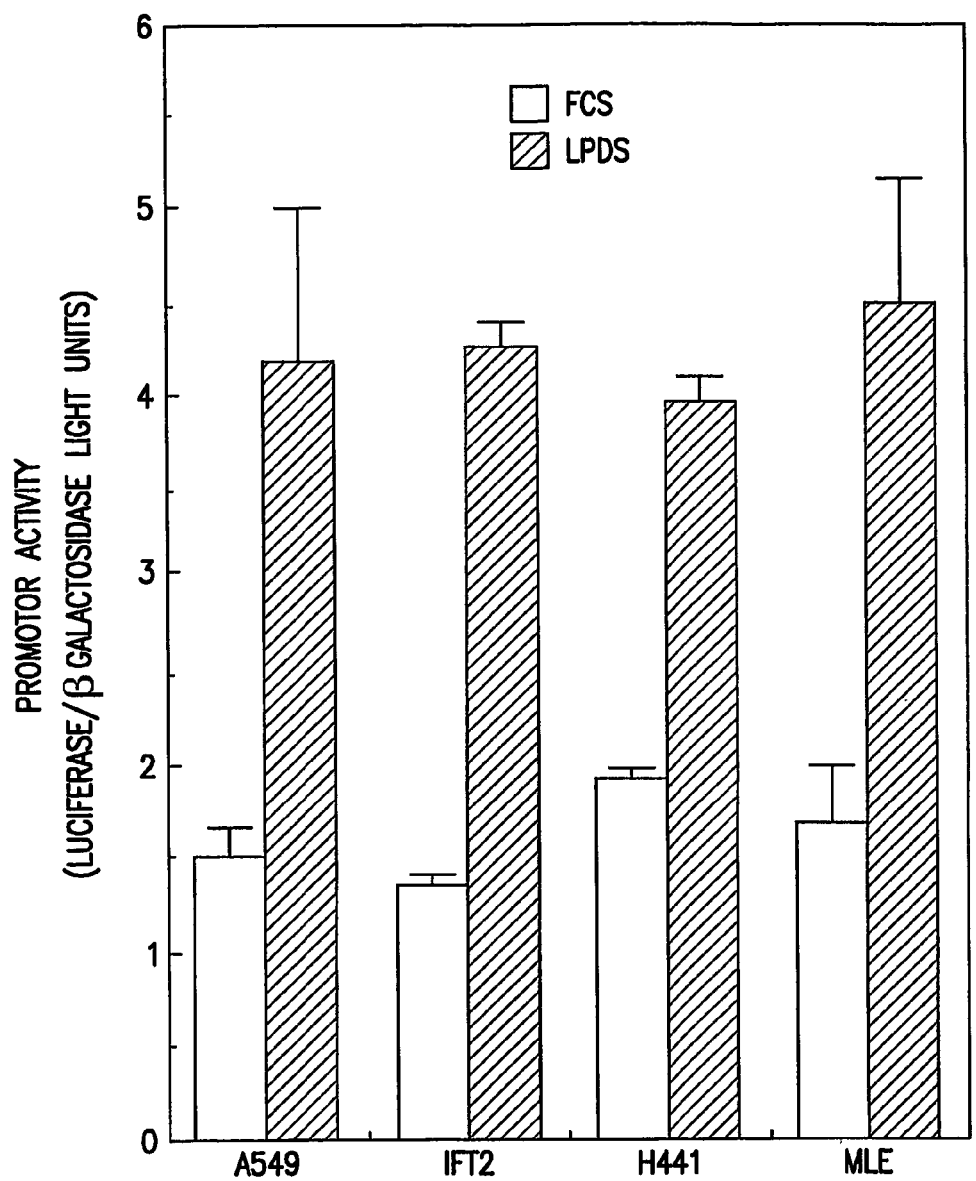
FIG. 6 shows that LPDS activation of the CCT promoter is not species specific.

LPDS Activation of the CCT Promoter is Not Species Specific (FIG. 6). Transfections conditions were identical to those described in FIG. 5. Expression of the CCTp240 experimental vector in the murine (MLE-12) type 2 cell line was compared to human (A549, and H441), and an immortalized fetal rat (IFT2) cell line. After transfections cells were exposed to medium containing FBS of LPDS and values normalized for transfection efficiency as in FIG. 4. The data is from of n=3 separate studies.

Figure 7:
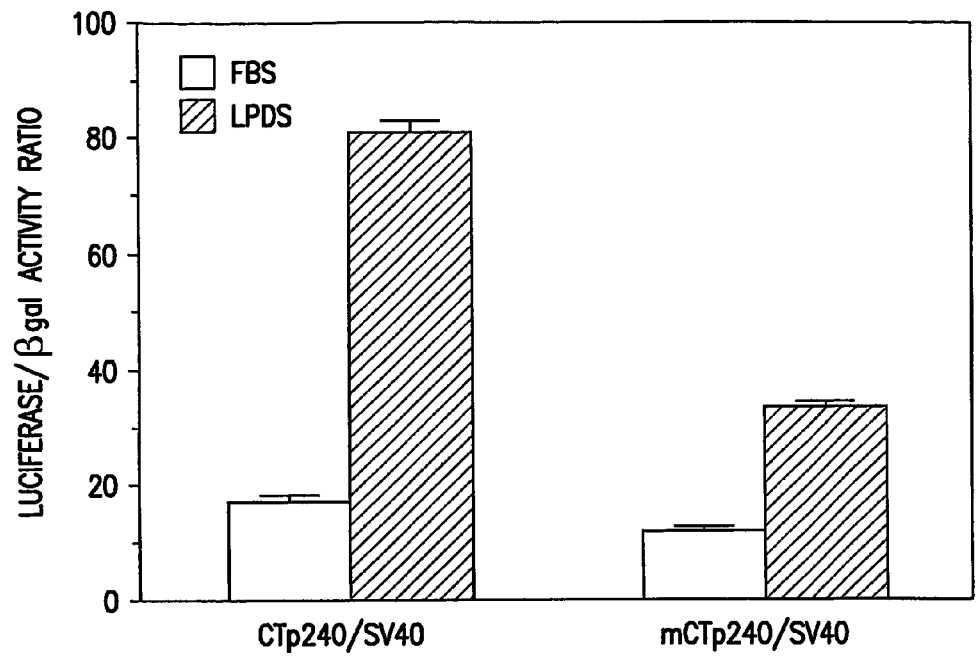
FIG. 7 shows that LPDS activation of the CCT promoter requires intact SRE.

LPDS Activation of the CCT Promoter Requires Intact SRE (FIG. 7). Transfections conditions were identical to those described in FIG. 5. MLE cells were transfected with a wild-type or mutated CCTp240 experimental vector where the SRE element was modified. The putative sterol regulatory element (SRE) within the 5' flanking region (−156/−147 bp relative to first transcriptional start site) of the CCT gene, GTCACCCCAC (SEQ ID NO:5), was mutated to GTAAACCCAC (SEQ ID NO:6) using the Quikchange Site-Directed Mutagenesis Kit (Stratagene, La Jolla, Calif.) and primers 5'-CCGCTCAGTAAACCCACGCGCCCGG-3' (left) (SEQ ID NO:7) and 5'-CCGGGCGCGTGGGTT-TACTGAGCCG-3' (right) (SEQ ID NO:8). After transfections cells were exposed to medium containing FBS or LPDS and values normalized for transfection efficiency as in FIG. 4. The data is from of n=3 separate studies.

Figure 8:
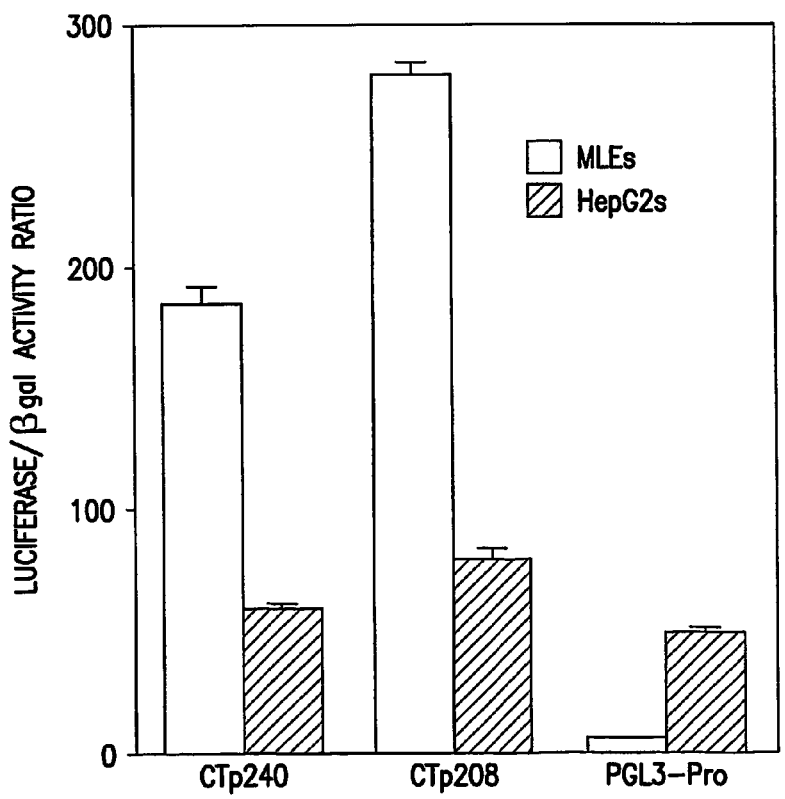
FIG. 8 shows the promoter activity of CCT.

Promoter Activity of CCT (FIG. 8). A murine lung epithelial (MLE) cell line (closed bars) or a hepatoma (HepG2) line (hatched bars) were transfected with one of three different promoter constructs: 1) a 240 bp promoter fragment of the CCT gene (CCTp240), 2) a novel 208 bp promoter fragment of the CCT gene, or 3) an SV40 strong viral promoter. Transfections were conducted for 90 min in Fugene 6 with Hites 0.5% fetal bovine serum. After 18 hrs, cells were harvested and luciferase and β galactosidase activities assayed. Luminometer readings were normalized for transfection efficiency by co-transfection of CMV-β galactosidase. Similar results were observed in two additional studies.

Figure 9:
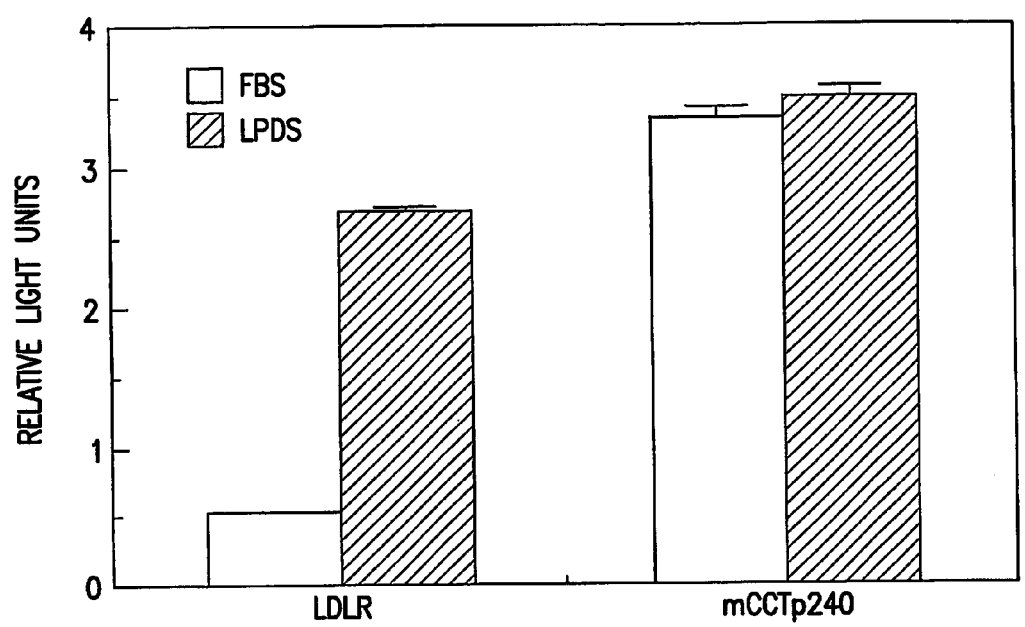
FIG. 9 shows that LPDS activates the CCT promoter in MLE cells.

LPDS Activates the CT Promoter in MLE Cells (FIG. 9). Transfections were conducted as in FIG. 6. After transfections, cells were exposed to medium containing 10% FBS or LPDS for 18 hr. For comparison, the effects of LPDS on activation of a positive control plasmid encoding the human low-density lipoprotein receptor (LDLR) coupled to luciferase were tested. The effects of LPDS on a CCT promoter luciferase construct harboring mutations within the candidate sterol-regulatory element (mCCTp240) were also tested. Luciferase and β-galactosidase activities in cellular extracts were determined in a luminometer. The data is representative of n=6 separate studies (inset n=3). Thus, FIG. 9 shows that the mCCTp240 promoter is considerably stronger than the commonly used LDLR promoter.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. An isolated and purified DNA CTP:phosphocholine cytidylyltransferase (CCT) p208 promoter or a mutant CCT p240 promoter consisting of DNA which is at least 95% identical to SEQ ID NO: 1 or SEQ ID NO: 2, and wherein the DNA exhibits at least a 2-fold increase in expression above a PGL3Pro promoter.

2. The promoter of claim 1, wherein the DNA exhibits at least a 10-fold increase in expression above a PGL3Pro promoter.

3. The promoter of claim 1, wherein the DNA exhibits at least a 20-fold increase in expression above a PGL3Pro promoter.

4. The promoter of claim 1, wherein the DNA exhibits at least a 30-fold increase in expression above a PGL3Pro promoter.

5. An expression cassette comprising a first preselected DNA segment that comprises the promoter of claim 1 that is functional in a host cell and is operably linked to a second preselected DNA segment encoding a protein, RNA transcript, or a combination thereof.

6. The expression cassette of claim 5, which further comprises an enhancer element.

7. The expression cassette of claim 5, wherein the second preselected DNA segment comprises a selectable marker gene or a reporter gene.

8. The expression cassette of claim 5, wherein the host cell is a eukaryotic cell.

9. The expression cassette of claim 8, wherein the host cell is an animal cell.

10. The expression cassette of claim 8 wherein the host cell is a mammalian cell.

11. The expression cassette of claim 8 wherein the host cell is a human cell.

12. The expression cassette of claim 8 wherein the host cell is a plant cell.

13. A method for producing transformed cells comprising the steps of (i) introducing into cells a recombinant DNA which comprises a promoter of claim 1 operably linked to a DNA segment so as to yield transformed cells, and (ii) identifying or selecting a transformed cell line.

14. The method of claim 13, wherein the recombinant DNA is expressed so as to impart a phenotypic characteristic to the transformed cells.

15. The method of claim 13, wherein the DNA segment comprises a selectable marker gene or a reporter gene.

16. The transformed cell made by the method of claim 13.

17. An isolated host cell comprising the isolated and purified DNA molecule of claim 1.

18. An isolated host cell comprising the expression cassette of claim 5.

* * * * *

UNITED STATES PATENT AND TRADEMARK OFFICE
CERTIFICATE OF CORRECTION

| | |
|---|---|
| PATENT NO. | : 7,230,091 B2 |
| APPLICATION NO. | : 10/488438 |
| DATED | : June 12, 2007 |
| INVENTOR(S) | : Rama K. Mallampalli |

It is certified that error appears in the above-identified patent and that said Letters Patent is hereby corrected as shown below:

On the cover page, item 57, line 1 delete "noveal" and insert --novel--.

On the cover page, item 57, lines 3 - 4, delete "cytidylyltrransferase" and insert --cytidylyltransferase--.

In column 23, line 37, in claim 1, delete "DNA".

Signed and Sealed this

Twenty-seventh Day of November, 2007

JON W. DUDAS
*Director of the United States Patent and Trademark Office*